Figure 2:
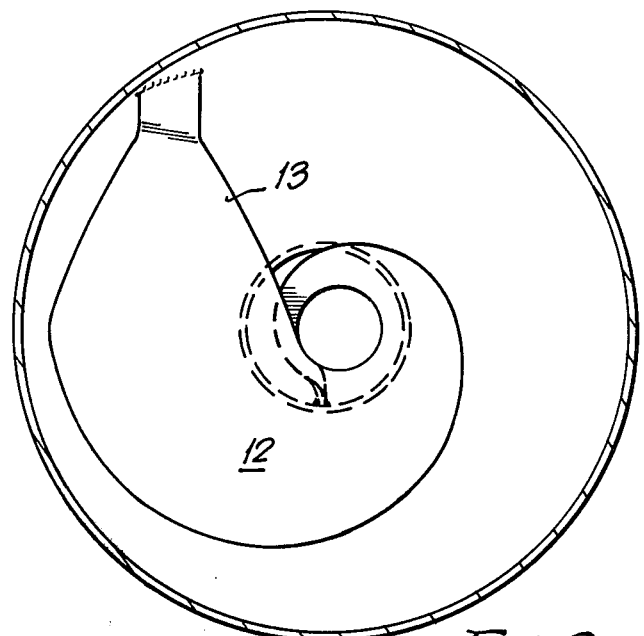

United States Patent [19]
Watson

[11] 3,940,037
[45] Feb. 24, 1976

[54] DISCHARGE FROM HOPPERS

[75] Inventor: Lewis Ainsley Watson, Caarbrook, England

[73] Assignee: Simon-Carves Ltd., Cheshire, England

[22] Filed: June 21, 1974

[21] Appl. No.: 481,739

[30] Foreign Application Priority Data
July 20, 1973 United Kingdom............... 34814/73

[52] U.S. Cl.................................. 222/564; 193/12
[51] Int. Cl.² ........................................... B67D 3/00
[58] Field of Search........... 222/459, 564; 214/17 C, 214/17 R, 17 A; 193/12, 13; 141/331, 333, 334, 339

[56] References Cited
UNITED STATES PATENTS

| | | | |
|---|---|---|---|
| 1,317,771 | 10/1919 | Adams | 214/17 R |
| 1,928,459 | 9/1933 | Pardee | 214/17 R |
| 3,278,054 | 10/1966 | Stott | 214/17 C |

FOREIGN PATENTS OR APPLICATIONS

| | | | |
|---|---|---|---|
| 651,600 | 11/1962 | Canada | 193/12 |
| 740,093 | 10/1943 | Germany | 193/12 |

Primary Examiner—Allen N. Knowles
Attorney, Agent, or Firm—Norris & Bateman

[57] ABSTRACT

A device for facilitating the discharge of material from a hopper of the kind whose cross-sectional area in a horizontal plane reduces gradually over at least the lower part of the hopper towards the outlet thereof comprising a helical blade rigidly secured within the hopper, the blade being so dimensioned and arranged as to impart a circular component of motion to the material as it runs through the lower regions of the hopper towards the outlet thereof.

19 Claims, 2 Drawing Figures

U.S. Patent   Feb. 24, 1976   3,940,037

DISCHARGE FROM HOPPERS

This invention concerns a device for facilitating the discharge of materials under the influence of gravity from hoppers of the kind (hereinafter termed of the kind referred to) whose cross-sectional area in a horizontal plane reduces gradually over at least the lower part of the hopper towards the outlet thereof.

The device is particularly, though by no means exclusively, suitable for use in the discharge of pre-heated coal from the hoppers of a charging machine into the oven chambers of a coke oven battery.

As is well known, coke oven chambers are usually charged from a machine having a plurality of hoppers of the kind referred to and adapted to hold coking coal, the machine being arranged for movement over the roof of a coke oven battery whereby such hoppers can be aligned over chargeholes giving access to the individual oven chambers. It is now becoming common to charge coke oven chambers with coal which has been pre-heated. This pre-heated coal has a high tendency to form bridges in the hoppers making discharge from the hoppers difficult and time-consuming.

I have noticed that if pre-heated coal is fed into an oven chamber with sufficient velocity it behaves like a fluid and finds a substantially common level within the oven chamber, making mechanical levelling unnecessary.

It is an object of the present invention to provide means to overcome or at least reduce the tendency for pre-heated coal to form a bridge in the hopper. In this way the coal falls freely and attains a substantial velocity, as it flows from the hopper under the influence of gravity, which can be sufficient to impart the self-levelling characteristics referred to above.

According to the present invention, a device for facilitating the discharge of material from a hopper of the kind referred to comprises a helical blade rigidly secured within the hopper, the blade being so dimensioned and arranged as to impart a circular component of motion to the material as it runs through the lower regions of the hopper towards the outlet thereof.

The invention will be further apparent from the following description with reference to the figures of the accompanying drawing which show, by way of example only, one form of device embodying the invention.

Figure 1:
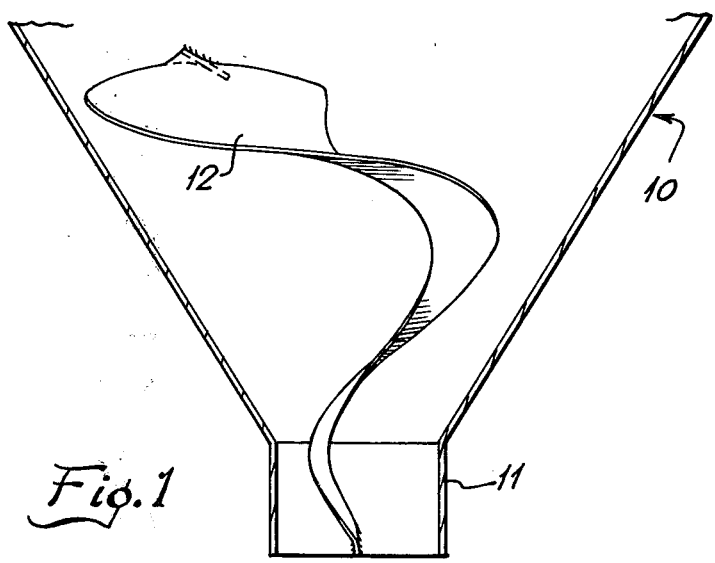

Of the drawing:

FIG. 1 is a cross-section through the lower regions of a hopper showing a side view of the device located therein;

and FIG. 2 is a plan view of the device of FIG. 1, in a position within the hopper.

Referring now to the drawing, it will be seen that the hopper, generally indicated by the reference numeral 10, is of circular cross-section in the horizontal plane. The lower region of the hopper is of inverted conical form whereby the area of cross-section reduces gradually to an outlet orifice defined by a short length of cylindrical tube 11 disposed with its central axis in a vertical direction. As shown the inner surface of the hopper is symmetrical about the central vertical axis of the hopper.

The device of the invention essentially comprises a helical blade 12 which is secured within the hopper 10. The helical blade 12 comprises in this example, one and a quarter turns, the inner edge thereof lying on the surface of an imaginary cylinder whose central axis is parallel with the central vertical axis of the hopper 10 but laterally offset therefrom. The width of the blade decreases gradually from a maximum at its upper end to zero at its extreme lower end, and pitch of the helix increases gradually from the upper end of the blade to its lower end.

As best seen from FIG. 2 the helical blade 12 is integrally formed with a tongue 13 which extends from the upper end of the blade towards the wall of the hopper 10.

The tongue 13 is twisted through an angle of approximately 45° and its free end is welded to the wall of the hopper 10. The extreme lower end of the helical blade 12 contacts the wall of the tube 11 and is welded thereto. In this way, the blade 12 is rigidly secured within the hopper, and it will be noted that there is a clearance between the outer edge of the blade 12 and the inner surface of the wall of the hopper 10 over most of the length of the blade 12.

In use, during discharge of material from the hopper such material flows past the helical blade 12. Passage over and past the blade 12 causes a circular component of motion to be imparted to the material thereby reducing if not eliminating bridging of the material in the lower regions of the hopper.

Furthermore, the helical blade causes the material to accelerate as it approaches the outlet to the hopper thereby increasing the specific volume of the material which again reduces the danger of bridging in the critical zone of reduced cross-sectional area at the outlet from the hopper.

Preferably the helical blade is formed from polished stainless steel and the edges thereof are sharpened.

Tests with a hopper incorporating a device embodying the invention have shown that pre-heated coal can be discharged very much more rapidly than from a hopper not incorporating the device and with the danger of bridging substantially reduced, if not eliminated, and with sufficient speed to ensure that the coal finds a substantially common level within the oven chamber.

It will be appreciated that it is not intended to limit the invention to the above example only, many variations, such as might readily occur to one skilled in the art, being possible without departing from the scope thereof, as defined by the appended claims.

What is claimed is:

1. In combination with a hopper at least the lower part of which is symmetrical about a substantially central vertical axis and whose cross-sectional area reduces gradually over said lower part toward an outlet, a device for facilitating the discharge of material from said hopper comprising a helical blade rigidly secured to extend in the direction of said axis within said lower part of the hopper, said blade being so constructed and arranged as to impart a circular component of motion to the material as it runs through the lower part of the hopper towards the outlet and the width of said blade decreasing gradually from a maximum at its upper end to a minimum at its lower end.

2. In combination with a hopper at least the lower part of which is symmetrical about a substantially central vertical axis and whose cross-sectional area reduces gradually over said lower part toward an outlet, a device for facilitating the discharge of material from said hopper comprising a helical blade rigidly secured to extend in the direction of said axis within said lower part of the hopper, the blade being so constructed and arranged as to impart a circular component of motion so the material as it runs through the lower part of the hopper towards the outlet, and the inner edge of said helical blade lying on the surface of an imaginary cylinder whose central axis is parallel with the central vertical axis of said hopper.

3. The combination according to claim 2 wherein the central axis of said imaginary cylinder is laterally offset from the central vertical axis of the hopper.

4. The combination according to claim 2 wherein the width of the helical blade decreases gradually from a maximum at its upper end to a minimum at its lower end.

5. The combination according to claim 2 wherein the width of the helical blade decreases gradually from a maximum at its upper end to a minimum at its lower end.

6. The combination according to claim 4 wherein the width of the helical blade reduces to zero at its extreme lower end.

7. The combination according to claim 5 wherein the width of the helical blade reduces to zero at its extreme lower end.

8. The combination according to claim 1 wherein the pitch of the helix of the helical blade increases gradually from the upper end thereof to the lower end thereof.

9. The combination according to claim 7 wherein the pitch of the helix of the helical blade increases gradually from the upper end thereof to the lower end thereof.

10. The combination according to claim 1 wherein there is a clearance between the outer edge of the blade and the inner surface of the wall of the hopper over most of the length of the blade, the blade being secured to the wall of the hopper at its upper and lower ends.

11. The combination according to claim 9 wherein there is a clearance between the outer edge of the blade and the inner surface of the wall of the hopper over most of the length of the blade, the blade being secured to the wall of the hopper at its upper and lower ends.

12. The combination according to claim 10 wherein the helical blade is integrally formed with a tongue at its upper end which extends from the blade and which is secured to the wall of the hopper.

13. The combination according to claim 11 wherein the helical blade is integrally formed with a tongue at its upper end which extends from the blade and which is secured to the wall of the hopper.

14. The combination according to claim 12 wherein said tongue is twisted through an angle of approximately 45°.

15. The combination according to claim 13 wherein said tongue is twisted through an angle of approximately 45°.

16. The combination according to claim 1 wherein the helical blade has one and one quarter turns or thereabouts.

17. The combination according to claim 15 wherein the helical blade has one and one quarter turns or thereabouts.

18. The combination according to claim 1 wherein said helical blade is formed from stainless steel.

19. The combination according to claim 1 wherein the edges of the helical blade are sharpened.

* * * * *